United States Patent
Sayani et al.

(10) Patent No.: US 10,244,985 B1
(45) Date of Patent: Apr. 2, 2019

(54) WEARABLE DIAGNOSTIC DEVICE

(71) Applicant: Saleem Sayani, King of Prussia, PA (US)

(72) Inventors: Saleem Sayani, King of Prussia, PA (US); Muhammad Abdul Muqeet, Karachi (PK); Hafiz Imtiaz Ahmed, Karachi (PK)

(73) Assignee: Saleem Sayani, King of Prussia, PA (US)

( * ) Notice: Subject to any disclaimer, the term of this patent is extended or adjusted under 35 U.S.C. 154(b) by 0 days.

(21) Appl. No.: 15/856,504

(22) Filed: Dec. 28, 2017

(51) Int. Cl.
| | | |
|---|---|---|
| *A61B 5/11* | (2006.01) | |
| *A61B 5/00* | (2006.01) | |
| *A61B 5/024* | (2006.01) | |
| *A61B 5/0205* | (2006.01) | |

(52) U.S. Cl.
CPC ............ *A61B 5/681* (2013.01); *A61B 5/11* (2013.01); *A61B 5/742* (2013.01); *A61B 5/0006* (2013.01); *A61B 5/0008* (2013.01); *A61B 5/0024* (2013.01); *A61B 5/0205* (2013.01); *A61B 5/02438* (2013.01)

(58) Field of Classification Search
CPC .......... A61B 5/681; A61B 5/11; A61B 5/742; A61B 5/0006; A61B 5/0008; A61B 5/0024
USPC ................................................. 600/300–301
See application file for complete search history.

(56) References Cited

U.S. PATENT DOCUMENTS

| | | | |
|---|---|---|---|
| 5,012,229 A | 4/1991 | Lennon | |
| 8,328,718 B2 | 12/2012 | Tran | |
| 2014/0278229 A1* | 9/2014 | Hong | A63B 71/06 702/160 |
| 2014/0316220 A1* | 10/2014 | Sheldon | A61B 5/0205 600/301 |
| 2015/0112606 A1 | 4/2015 | He | |
| 2016/0120460 A1 | 5/2016 | Eom | |
| 2016/0157733 A1* | 6/2016 | Gil | A61B 5/0402 600/301 |
| 2016/0162256 A1 | 6/2016 | Komaromi | |
| 2017/0055891 A1 | 3/2017 | Chaychi | |
| 2017/0332980 A1 | 11/2017 | Fifield | |

OTHER PUBLICATIONS

International Search Report and Written Opinion for PCT/US2017/068692 dated Aug. 28, 2018, 14 pages.

* cited by examiner

*Primary Examiner* — Carl H Layno
*Assistant Examiner* — Dacheng Xie
(74) *Attorney, Agent, or Firm* — Fish & Richardson P.C.

(57) ABSTRACT

A wearable diagnostic device worn on a user's body that can provide various types of health-related information to the user is described. The wearable diagnostic device can provide real-time, non-invasive, accurate, and continuous data regarding a user's heart rate, hemoglobin level, body temperature, oxygen level, glucose level, and blood pressure. In some implementations, the wearable diagnostic device may also provide electrocardiogram (EKG) data or detection of Parkinson's symptoms, such as the involuntary movement of a user's hand. A user may configure the wearable diagnostic device to provide information on one, multiple, or all of the health-related information noted above.

20 Claims, 13 Drawing Sheets

WEARABLE DIAGNOSTIC DEVICE

BACKGROUND

With individuals becoming increasingly health conscious, there is a growing demand amongst users for receiving personal health information in a simple and convenient manner. Often users may have to wear multiple devices that each provide information on a single aspect of the user's health. There is a need for a device that can provide information regarding multiple aspects or a user's health in a simple, non-invasive, and convenient manner.

SUMMARY

In general, innovative aspects of the subject matter describe a wearable diagnostic device and methods and systems for performing one or more medical diagnostic tests.

In some implementations, a system includes one or more computer devices and one or more storage devices storing instructions which when executed by the one or more computer devices, cause the one or more computer devices to perform operations. The operations include receiving an input corresponding to a request to begin a non-invasive diagnostic test to detect a medical state of a user, identifying one or more sensors for conducting the non-invasive diagnostic test, activating the identified one or more sensors based on the non-invasive diagnostic test, receiving signal data through the one or more sensors, obtaining a predicted value for the non-invasive diagnostic test based, in part, on a user profile, determining a test result based on the predicted value and the received signal data, and outputting, through a display or a speaker, the test result.

Implementations may each optionally include one or more of the following features. For instance, in some implementations, the non-invasive diagnostic test includes one or more of a glucose test, a cholesterol test, a hemoglobin test, an oxygen saturation level test, and an electrocardiogram monitoring test.

In some implementations, the operations further include selecting a pathway based on raw data obtained from the received signal data, and obtaining a set of determined values based on the selected pathway. Determining the test result based on the predicted value and the received signal data includes determining the test result based on the determined values.

In some implementations, the operations further include obtaining user clinical data and user demographic data from one or more databases, determining a clinical dataset range based on the obtained user clinical data and the user demographic data, and mapping the clinical dataset range to the predicted value for the non-invasive diagnostic test.

In some implementations, the operations further include determining a second non-invasive diagnostic test to be conducted based on (i) a user pattern of associating the second non-invasive diagnostic test with the non-invasive diagnostic test, and (ii) a medical history of the user; activating a second set of one or more sensors based on the second non-invasive diagnostic test; receiving second signal data through the second set of one or more sensors; obtaining a second predicted value for the second non-invasive diagnostic test based, in part, on the user profile; and determining a second test result based on the second predicted value and the received second signal data.

In some implementations, obtaining the predicted value for the non-invasive diagnostic test includes determining the predicted value for the non-invasive diagnostic test using the second test result.

In some implementations, the second non-invasive diagnostic test is a cholesterol test conducted simultaneously as the non-invasive diagnostic test that is a glucose test.

In some implementations, the non-invasive diagnostic test and the second non-invasive diagnostic test are conducted by a watch including the one or more computer devices.

In some implementations, the one or more sensors include one or more of a wireless cardiac electrode, a piezo vibration sensor, an infrared sensor, a temperature sensor, an accelerometer, and a micro-electro mechanical system (MEMS) sensor.

According to aspects of the disclosed subject matter, a watch includes one or more computer devices and one or more storage devices storing instructions which when executed by the one or more computer devices, cause the one or more computer devices to perform operations. The operations include selecting, based on a user profile, a glucose test and a cholesterol test, identifying one or more sensors for conducting the glucose test and the cholesterol test, activating the identified one or more sensors, receiving signal data through the one or more sensors, obtaining a first predicted value for the glucose test based, in part, on the user profile, determining a glucose test result and a cholesterol test result based on the first predicted value and the received signal data, and outputting, through a display or a speaker of the watch, the glucose test result and the cholesterol test result.

In some implementations, the one or more sensors include an infrared sensor and a piezo vibration sensor. The operations include selecting a pathway based on raw data obtained from the received signal data, and obtaining a set of determined values based on the selected pathway. Determining the glucose test result based on the first predicted value and the received signal data includes determining the glucose test result based on the determined values.

The above-noted aspects and implementations further described in this specification offer several advantages. For instance, a single wearable diagnostic device may conduct multiple non-invasive diagnostic tests including non-invasive glucose testing, non-invasive cholesterol testing, and non-invasive hemoglobin testing. The wearable diagnostic device may also obtain electrocardiogram (EKG) data or detection of Parkinson's symptoms, such as the involuntary movement of a user's hand. The wearable diagnostic device with wireless electrodes may keep track of user history and medical conditions, and may utilize predictive values, algorithms, and mapping databases to provide higher accuracy and reliable results for glucose, cholesterol, and/or hemoglobin tests. The predictive values include the user's clinical and demographic information and can therefore make calculations that factor in parameters such as skin color and age, which may affect glucose or hemoglobin levels, more accurate. The predictive values may also be used to correlate the predictive values to the user's susceptibility to certain diseases.

Other aspects include corresponding methods, systems, apparatus, computer-readable storage mediums, and computer programs configured to implement the actions of the above-noted methods.

The details of one or more aspects described in this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

This disclosure generally relates to a wearable diagnostic device that may be worn on a user's body to provide various types of health-related information to the user. In some implementations, the wearable diagnostic device may perform one or more medical diagnostic tests and provide real-time, non-invasive, accurate, and continuous data regarding a user's heart rate, hemoglobin level, body temperature, oxygen level, glucose level, cholesterol, and blood pressure. In some implementations, the wearable diagnostic device may also provide electrocardiogram (EKG) data and detection of Parkinson's symptoms, such as the involuntary movement of a user's hand. A user may configure the wearable diagnostic device to provide information on one or more of the above-noted diagnostic tests. Implementations of the wearable diagnostic device are described below with reference to the figures.

Figure 1:
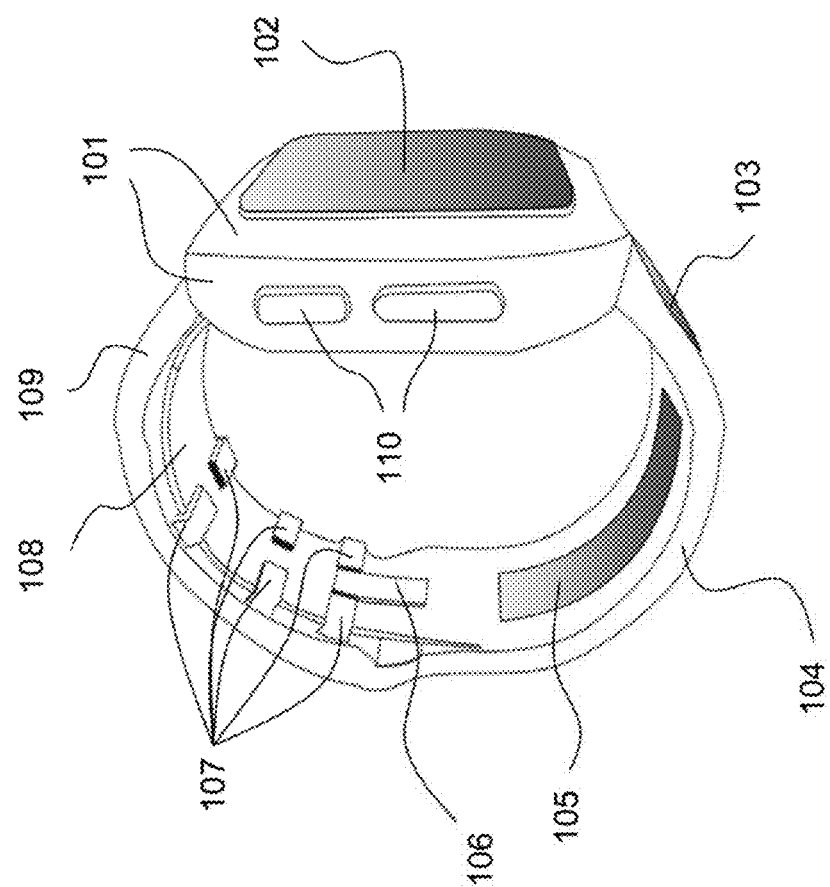
FIGS. 1, 2, 3, 4, and 5 depict exemplary implementations of a wearable diagnostic device.
Figure 2:
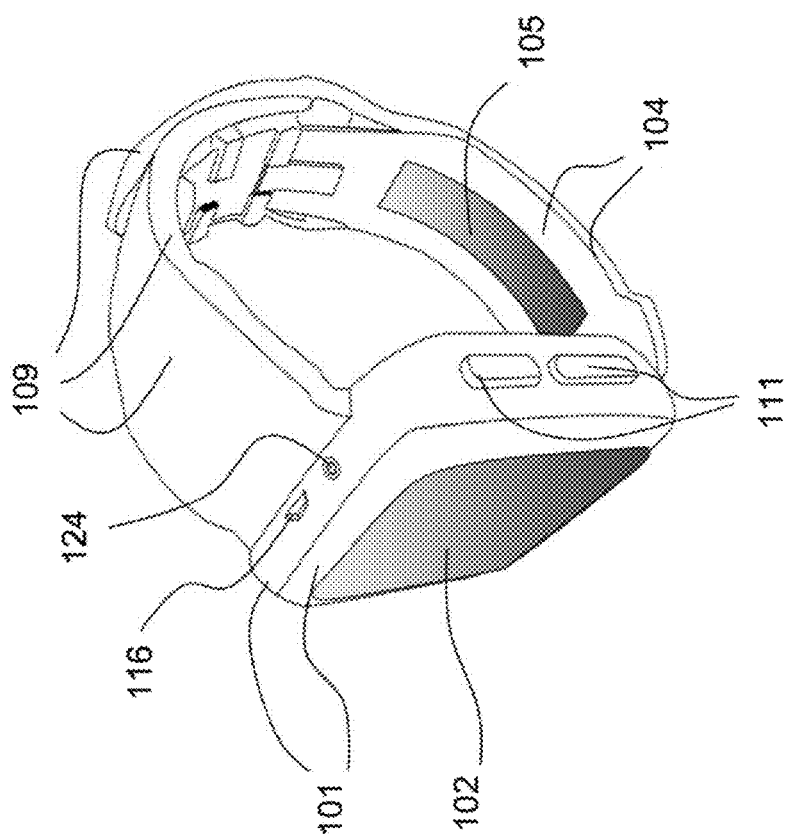
Figure 3:
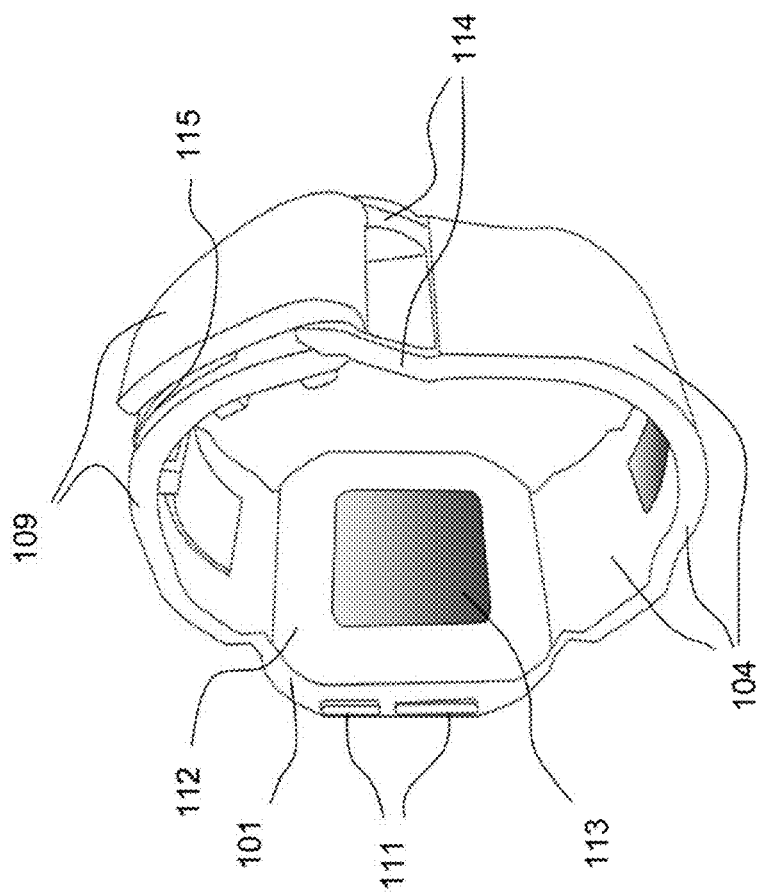
Figure 4:
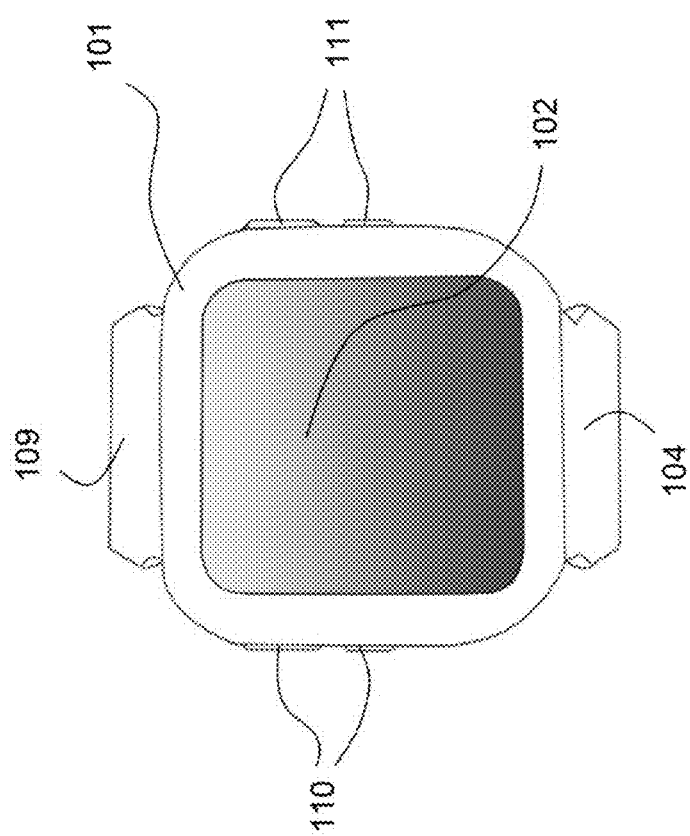
Figure 5:
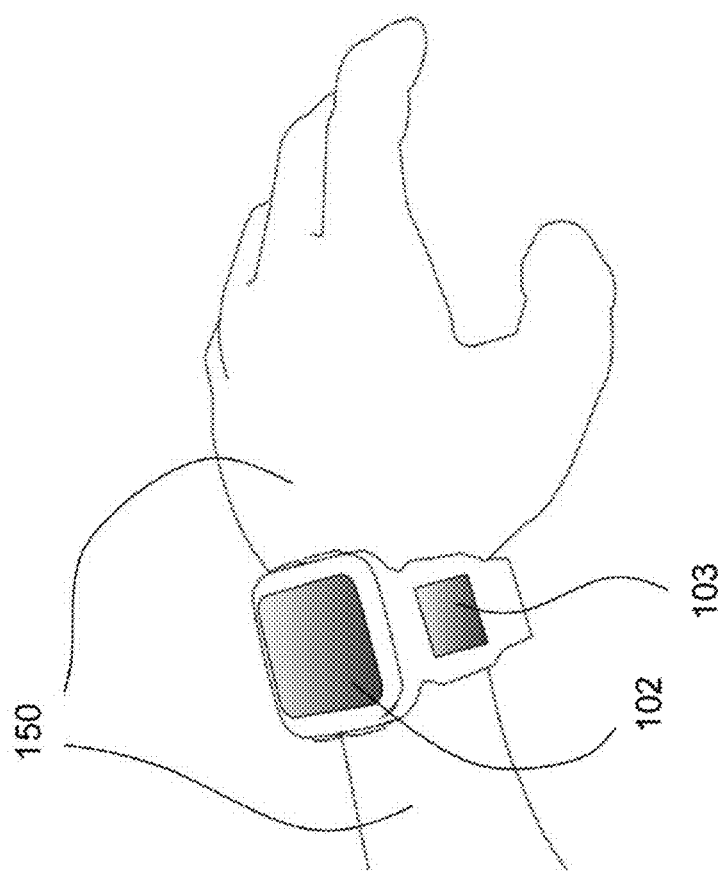
Figure 6:
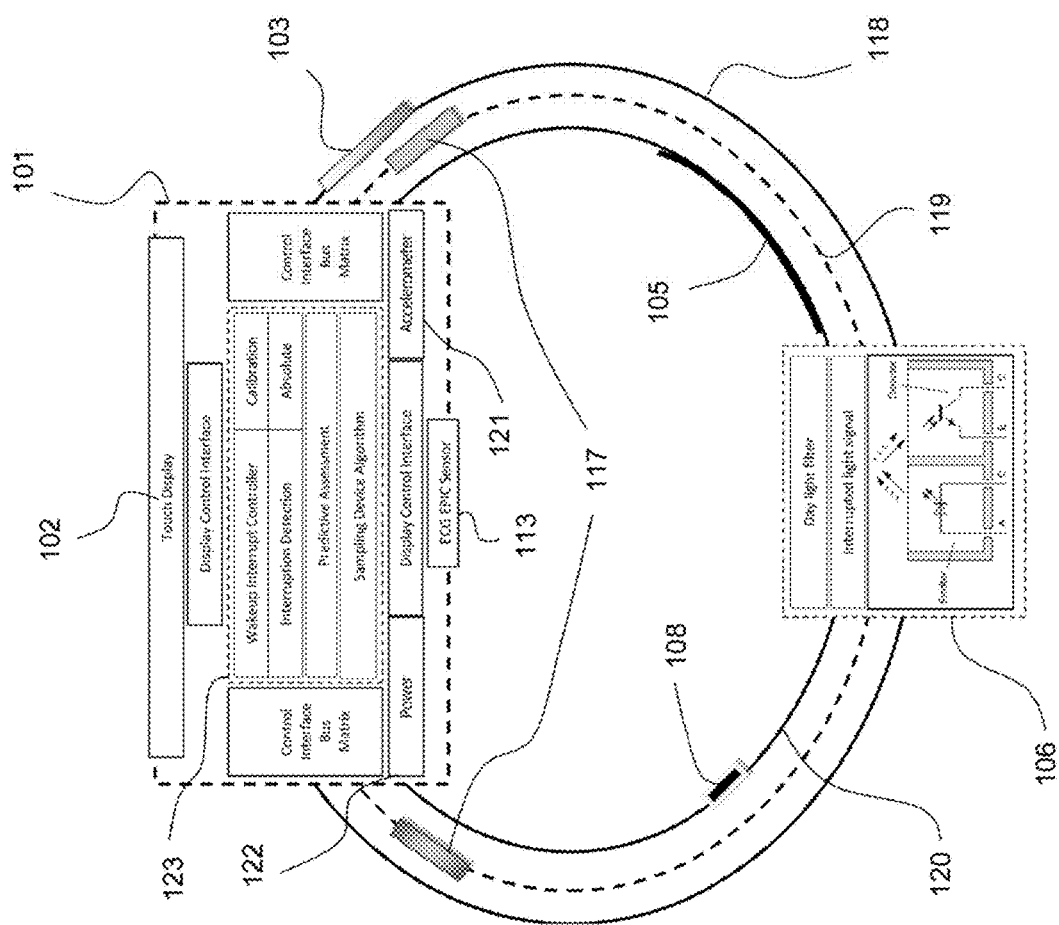
FIG. 6 depicts an exemplary system implemented in a wearable diagnostic device.

FIGS. 1-5 illustrate different views of a wearable diagnostic device. In some implementations, the wearable diagnostic device may be implemented in the form of a watch, as shown in FIGS. 1-5. FIG. 6 depicts additional details of the components included in the wearable diagnostic device according to some implementations. In general, the wearable diagnostic device may be implemented in various suitable shapes, forms, and sizes, and may be any electronic device that can be attached to a user's left arm and is capable of obtaining multiple health diagnostic measurements for the user.

Referring to FIGS. 1-5, the wearable watch may include a casing 101, a display 102, detachable wireless cardiac electrodes 103, 113, a belt 104, 109, a piezo vibration sensor 105, an infrared (IR)/light/laser sensor 106, a connector 107, a temperature sensor 108, control buttons 110, 111, a rear cover 112, a belt connector 114, belt fastener 115, charging connector 116, power supply 117, outer belt layer 118, 120, insulated wire 119, accelerometer 121, power manager 122, system on chip (SoC) 123, and power switch 124. The wearable watch may be worn on a left arm 150 of a user.

Casing 101 may include or be coupled to display 102, charging connector 116, control buttons 110, 111, and one or more electronic components such as a processor, printed circuit board (PCB), integrated circuit (IC), SoC 123, memory, and wireless transceiver. Display 102 may be implemented using any suitable display including, for example, a liquid crystal display (LCD), light emitting diode (LED) display, or an organic LED display, to display various data. In some implementations, the display 102 may be a touch screen, such as a capacitive touch screen.

The display 102 may display a user interface configured to output data to a user and receive input from the user. Control buttons 110, 111 may be used by a user to navigate the user interface, make selections, and execute one or more operations in the wearable diagnostic device. In some implementations, display 102 may receive a selection from a user, and may provide information indicative of the user selection to one or more processors in the wearable watch or a network device. In some implementations, display 102 may receive data from the one or more processors, and may provide the data to the display 102 to output to the user. For example, in some cases, the user may input a request for providing the user's glucose levels through the user interface. After determining the user's glucose levels, information indicative of the user's glucose levels may be output through the user interface displayed on display 102.

One or more processors in casing 101 may be implemented in a PCB or IC and may be electrically connected to other electronic components of the wearable diagnostic device such as a memory, display 102, and wireless transceiver. For example, a processor may receive data indicative of a user selection from display 102, determine the type of information requested by the user, and generate commands to execute one or more operations based on the information requested by the user.

In some implementations, one or more processors may transmit and receive data using a wireless transceiver. Data may be transceived between the wearable diagnostic device and a secondary device. The secondary device may be a device selected by the user, a network server, or a device that the wearable watch is configured to communicate with. For example, the user may select another device owned by the user to send data from the wearable diagnostic device to. In another example, the wearable diagnostic device may be configured to transceive data to one or more network servers according to a user request or a predetermined schedule of transceiving data.

The one or more network servers may provide services for one or more networks, which may include one or more databases, access points, base stations, storage systems, cloud systems, and modules. The one or more servers may be a series of servers running a network operating system. The one or more servers may be used for and/or provide cloud and/or network computing.

The databases in the networks may include a cloud database or a database managed by a database management system (DBMS). A DBMS may be implemented as an engine that controls organization, storage, management, and retrieval of data in a database. DBMSs frequently provide the ability to query, backup and replicate, enforce rules, provide security, do computation, perform change and access logging, and automate optimization. A DBMS typically includes a modeling language, data structure, database query language, and transaction mechanism. The modeling language is used to define the schema of each database in the DBMS, according to the database model, which may include a hierarchical model, network model, relational model, object model, or some other applicable known or convenient organization. Data structures can include fields, records, files, objects, and any other applicable known or convenient structures for storing data. A DBMS may also include metadata about the data that is stored.

In some implementations, the databases may include a user database, which may store information of a user such as an alias name, a medical history, and any medical conditions of the user. The user database may also store data related to licenses, permissions, and certifications for accessing various tools and software. In some cases, the user may select an option to anonymize user data such that any information that can identify a user is anonymized and user identification information is removed prior to storing data in the user database.

In general, various suitable wireless protocols may be used to communicate data to and from the wearable diagnostic device. For example, the wearable diagnostic device may communicate with one or more networks, devices, or servers using WiFi or Bluetooth communications. In general, various types of networks may be communicated with and various communication protocols may be used.

Charging connector 116 may be a port configured to connect to a power supply cable such as a universal serial bus or conductive wire. Upon connecting to a power supply cable, the charging connector 116 may function as a power interface to provide power from an external source to charge the power supply 117 in the wearable watch. The power supply 117 may be any suitable battery, and may provide electrical power to any electrical component in the wearable diagnostic device.

Casing 101 also includes a power switch 124. In some implementations, in response to selection of the power switch 124 such that the power switch 124 is in a power off position, one or more processors may send a command to power manager 122 to stop providing electrical power to one or more components of the wearable diagnostic device, such as display 102. In some implementations, in response to selection of the power switch 124 such that the power switch 124 is in a power on position, the power manager 122 may send a command to power supply 117 to provide electrical power to one or more components of the wearable diagnostic device, such as display 102.

Casing 101 is connected to belts 104, 109, connector 107, and belt connector 114, which may be adjusted to secure the wearable diagnostic device around wrists of different sizes. For example, belts 104, 109 and belt connector 114 may be wrapped around a user's wrist, and a belt fastener 115 may hold the belts 104, 109 and belt connector 114 in a fixed position. A rear cover 112 and a cardiac electrode 113 may be disposed on a bottom portion of the casing 101.

One or more insulated wires 119 may be integrated into the structure of the wearable diagnostic device and may provide an electrical connection to various components of the wearable diagnostic device. For example, as illustrated in FIG. 6, one or more insulated wires 119 may be disposed along a central axis of the wearable diagnostic device and may provide an electrical connection between the power supply 117 and casing 101 and between the power supply 117 and the IR/light/laser sensor 106.

The wearable diagnostic device may also include one or more sensors such as cardiac electrodes 103, 113, a piezo vibration sensor 105, an infrared (IR)/light/laser sensor 106, a temperature sensor 108, an accelerometer 121, and an impedance sensor. In some implementations, the piezo vibration sensor 105 may include a micro-electro mechanical system (MEMS) sensor.

The wireless cardiac electrodes 103, 113 may include metallic conductive material configured to detect cardiac electrical potential waveforms, such as voltages produced during the contraction of the heart. Wireless cardiac electrode 103 is disposed on an outer belt layer 118 corresponding to an outer circumference of the wearable diagnostic device. Wireless cardiac electrode 113 is disposed on or integrated within the rear cover 112 so that it may contact the user's skin when the wearable diagnostic device is secured around a user's arm 150. The wireless cardiac electrodes 103, 113 may be detached and reattached to the wearable diagnostic device and may communicate data to another electronic device wirelessly.

IR/light/laser sensor 106 may include a signal generator and a signal detector. The signal generator may generate and transmit infrared signals having a wavelength in the range of, for example, 650-1400 nanometers (nm). This range is particularly useful to obtain data indicative of the presence of oxygen, glucose, hemoglobin molecules in the user's blood. The signal detector may be configured to detect infrared signals received from the user's body.

In some implementations, the IR/light/laser sensor 106 may detect pulse signals and process the detected signals using the Pulse Wave Transit Time (PWTT) in the Artery method. These pulse signals may be combined with data acquired by the piezo vibration sensor 105 to predict the blood pressure non-invasively. The IR/light/laser sensor 106 may also be used to determine or obtain data indicative of the oxygen saturation levels ($SpO_2$) in the user's blood non-invasively.

The piezo vibration sensor 105 and accelerometer 121 may be used to measure vibrations of the user's hand. For example, accelerometer 121 may detect changes in direction, velocity, vibrations, and rotations. A temperature sensor 108 may be used to measure the body temperature of the user. The temperature sensor 108 may be implemented in various suitable ways. For example, the temperature sensor 108 may be a thermocouple, a silicon bandgap sensor, a thermometer, or a thermistor comprising one or more sensing resistors. A change in electrical resistance in the sensing resistors may correspond to a change in body temperature. In some implementations, temperature sensors may include active and passive components and resistive and semiconductor material fabricated in a single package of ICs.

The sensors may be used to obtain one or more measurements as described in further detail below. Operations performed using the wearable diagnostic device to determine glucose levels, hemoglobin levels, blood pressure levels, EKG, heart rate levels, body temperature and hand vibrations are described in further detail below. The operations begin by the user placing the wearable diagnostic device on the user's left arm 150 and adjusting one or more of the belt 104, 109, belt connector 114, belt fastener 115, and outer belt layer 118, 120 to secure the wearable diagnostic device around the user's left arm 150.

When the wearable diagnostic device is secured on the user's left arm 150, the IR/light/laser sensor 106 may be in contact with an inferior part of the user's left wrist directly above the user's radial ulnar artery. As noted above, the IR/light/laser sensor 106 may include a signal generator to generate and transmit an infrared signal. The signal may be transmitted from the IR/light/laser sensor 106 towards the user's skin in the inferior part of the user's left wrist.

The IR/light/laser sensor 106 may detect a reflection of the signal from the user's skin. The detected signal including absorption spectra data may then be converted to a digital signal using an analog to digital converter (ADC). As a result of the conversion, raw digital data corresponding to the signal received from the user's skin is generated. The raw digital data can be processed to determine the absorption spectra corresponding to the presence of various molecules in the user's blood, such as oxygen, glucose, hemoglobin. By determining the absorption spectra, the existence and corresponding levels of particular molecules present in the user's blood may be estimated.

In some implementations, multiple signal measurements may be obtained so that multiple sets of raw digital data are obtained at various points of time. The different sets of raw digital data may be accumulated and averaged to yield a single set of raw data for the user.

In some implementations, the wearable diagnostic device may obtain information associated with the user's health. The information associated with the user's health may include, but is not limited to, for example, a user's residential location, a user's doctor, a user's pharmacist, a user's medical record holder, a user's demographic associations with one or more groups, a food diet of the user, an indication of a number of children the user has, a medical history of the user, one or more past or present medical conditions, for example, allergies, surgeries, genetic conditions, of the user, one or more health concerns of the user, and one or more blood content levels the user is interested in obtaining details about. For example, the user may indicate that the user is particularly interested in the user's glucose or blood pressure levels. The user may also indicate how often the user would like to obtain information about the user's glucose or blood pressure levels.

The information associated with the user's health may be used to create a user profile. The user profile may be stored locally in the wearable diagnostic device or in a database or server located remotely from the wearable diagnostic device. In some implementations, user profile data may be treated in one or more ways before it is stored or used, so that personally identifiable information is removed. For example, a user's identity may be treated so that no personally identifiable information can be determined for the user, or a user's geographic location, identity, or demographic background may be generalized to the extent a user desires so that particular details of the user cannot be determined. Thus, the user may have control over what information is collected and how that information is used. To implement this, the user may be provided with controls through the wearable diagnostic device that allow the user to elect if or when systems, programs, or features described herein may collect or provide user information.

In some implementations, the user may subscribe or elect to participate in a service through which the wearable diagnostic device may receive and be updated with the user's medical information in real time. In particular, the wearable diagnostic device may be updated with test results, doctor visit outcomes, diagnoses, or prescriptions. For example, the user may authorize the user's doctor, pharmacists, or medical record holder's to release the user's medical information to a server or database storing the user profile. This server or database may be managed through a subscription service, which may collect information from various sources to update the user's profile. The wearable diagnostic device may receive updates about the user's medical information in real time, periodically, or upon user request.

In some implementations, the user may directly input information regarding the user's health and background using a user interface of the wearable diagnostic device. The input user medical information may then be stored remotely or on the wearable diagnostic device.

It should be understood that although features described with respect to FIGS. 1-6 relate to the wearable diagnostic device being worn on the user's left arm, the wearable diagnostic device may have other varied forms and may, in some cases, be worn or applied on other parts of the user's body. Further, one or more additional components may be included in or coupled to the wearable diagnostic device. For example, in some implementations, the wearable diagnostic device may include one or more of a speaker to output information using a sound wave and a microphone to receive audio inputs corresponding to, for example, a user command, request, or feedback.

In some implementations, the wearable diagnostic device may be further configured to execute one or more diagnostic tests to obtain one or more of a glucose level, a hemoglobin level, or a blood pressure level associated with the user wearing the wearable diagnostic device based on received or obtained information associated with the user's health. These processes are described further in FIGS. 7-12.

Figure 7:
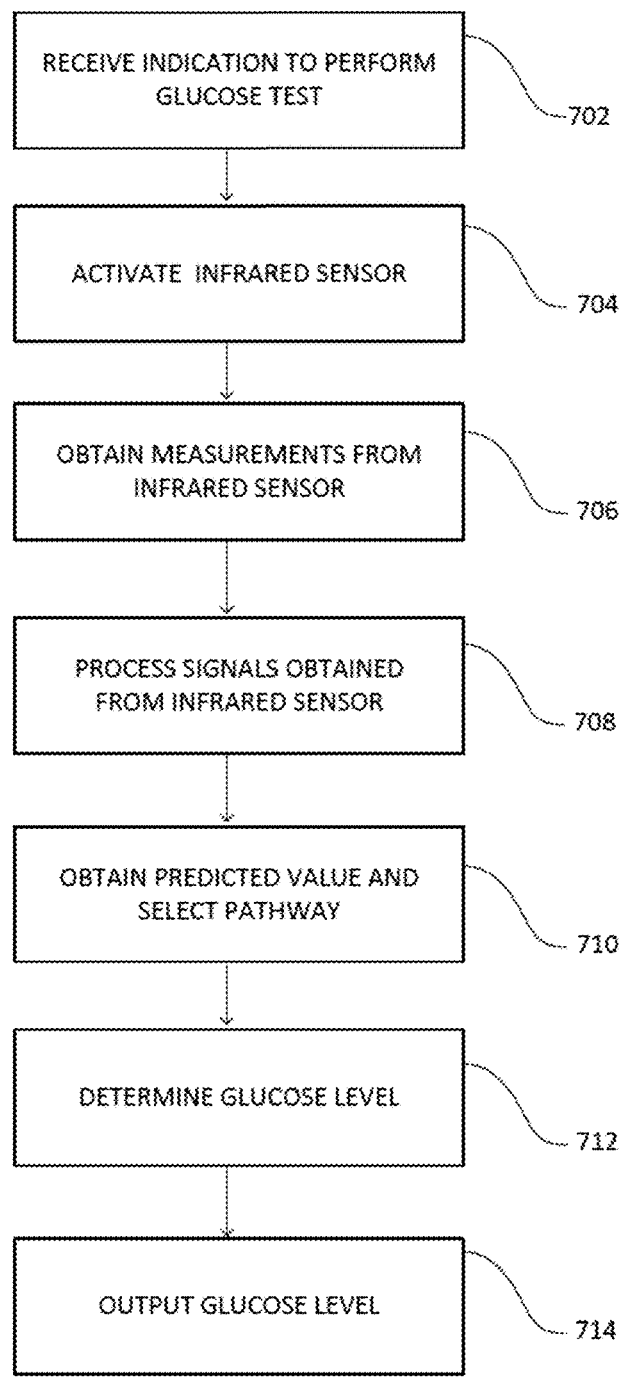
FIG. 7 depicts a flowchart of an exemplary method to determine a glucose level of a user.
Figure 9:
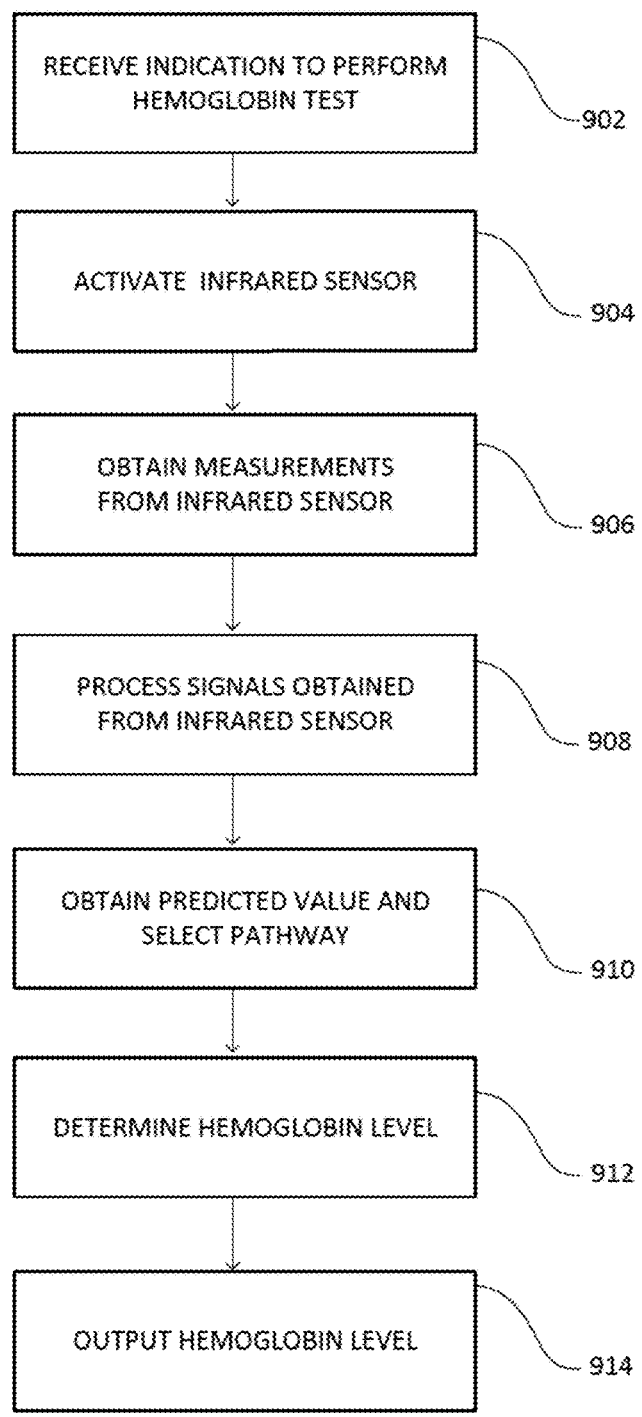
FIG. 9 depicts a flowchart of an exemplary method to determine a hemoglobin level of a user.
Figure 13:
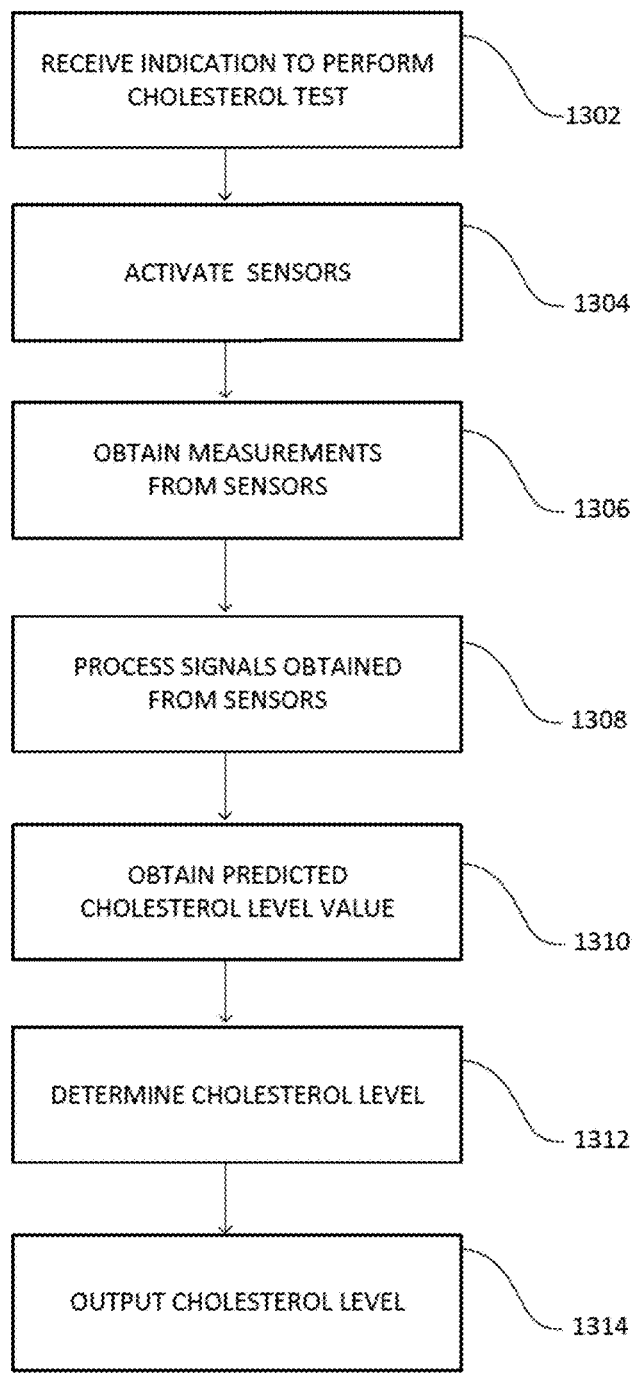
FIG. 13 depicts a flowchart of an exemplary method to determine a cholesterol level of a user.

Referring to FIGS. 7, 9, and 13, the wearable diagnostic device may receive an indication that a test should be performed (702, 902, 1302). For instance, the wearable diagnostic device may receive an indication that a glucose test (702), a hemoglobin test (902), or a cholesterol test (1302) should be performed. The indication that a test should be performed may include one or more of: a selection made by the user to conduct a test; and a request made by one or more processors according to a scheduled time. For example, the wearable diagnostic device may be programmed to provide a blood pressure reading at certain times or after certain time periods. The wearable diagnostic device may then schedule days and times when a particular reading, such as a blood pressure reading, should be provided to the user, and may initiate the method to determine blood pressure and oxygen saturation levels at the scheduled times.

After receiving the indication that a test should be performed (702, 902, 1302), the one or more processors of the wearable diagnostic device may determine the type of sensor utilized for the test and activate the determined type of sensors, which in the case of a glucose or hemoglobin test may include one or more IR/light/laser sensors (704, 904). In the case of a cholesterol test, the activated sensors may include one or more of an IR/light/laser sensor, an impedance sensor, and an electromagnetic sensor. Activating the sensors may include operations, including but not limited to, providing increased power to the sensors, warming up the sensors to emit or receive a signal, such as an IR signal, or configuring or calibrating the sensors.

The activated one or more sensors may obtain measurements characterizing the user (706, 906, 1306). For example, the one or more IR/light/laser sensors may be configured, respectively, to emit an infrared signal or a pulse signal for a short period of time, e.g., 30 seconds, and detect a reflection of the emitted signal from the user's skin. In some cases, reflection measurements and current measurements using an impedance sensor may be obtained iteratively or may be obtained under different environments, such as different pulse power or magnetic fields. For example, for cholesterol measurements, a first current or infrared signal measurement may be obtained without applying a magnetic field and one or more other current or infrared measurements may be taken after a magnetic field at various low power strengths is generated for a period of time, e.g., 10 seconds.

In the case of glucose and hemoglobin tests, the measured detected signals are processed and a particular pathway is selected based on the raw data values (708, 908). In particular, each of the detected signals include absorption spectra data that can be converted to raw digital data using an analog to digital converter (ADC). The processing may optionally include additional processing operations such as down conversion, filtering, convoluting, mixing, and any other suitable signal processing operation.

The raw digital data corresponding to the signal received from the user's skin is used as a basis to select a particular pathway and corresponding predictive values and slope regression values (710, 910). For example, when a glucose test is conducted, an exemplary mapping, as shown in TABLE I, may be used to select a particular pathway and corresponding predictive values and slope regression values. If the raw values are greater than or equal to 500 and less than or equal to 700, pathway A and a corresponding glucose (G) predictive value of 917 and G slope regression value of 0.838 are selected. If the raw values are greater than or equal to 701 and less than or equal to 850, pathway B and a corresponding G predictive value of 919 and G slope regression value of 0.838 are selected. If the raw values are greater than or equal to 851 and less than or equal to 950, pathway C and a corresponding G predictive value of 1001 and G slope regression value of 0.838 are selected. If the raw values are greater than or equal to 951 and less than or equal to 1100, pathway D and a corresponding G predictive value of 1004 and G slope regression value of 0.838 are selected. If the raw values are greater than or equal to 1101, pathway E and a corresponding G predictive value of 981 and G slope regression value of 0.838 are selected.

TABLE I

| Pathway | RAW DATA VALUE (X) | G PREDICTIVE VALUE | G SLOPE REGRESSION VALUE |
| --- | --- | --- | --- |
| A | 500 ≤ X ≤ 700 | 917 | 0.838 |
| B | 701 ≤ X ≤ 850 | 919 | 0.838 |
| C | 851 ≤ X ≤ 950 | 1001 | 0.838 |
| D | 951 ≤ X ≤ 1100 | 1004 | 0.838 |
| E | 1101 ≤ X | 981 | 0.838 |

The obtained predictive and slope regression values may then be used to determine a glucose level of the user (712). To determine a glucose level, the wearable diagnostic device may apply the Generalizability Theory and G slope regression to the set of raw data and determine values indicative of a glucose level using [Equation 1] as noted below.

$$\text{Glucose value} = \text{Predictive Values}_{(G\text{-clinical sampling regression})} - (G\text{Regression Slope})*(\text{Raw data}) \quad [\text{Equation 1}]$$

The determined glucose value may then be output through various suitable methods (714). For example, the determined glucose value may be output on a display of the wearable diagnostic device or output by a speaker of the wearable diagnostic device.

When a hemoglobin test is being conducted, an exemplary mapping as shown in TABLE II may be used to select a particular pathway and corresponding predictive values and slope regression values. If the raw values are equal to or greater than 500 and less than or equal to 700, pathway A and a corresponding Hemoglobin (Hb) predictive value of 31.5 and Hb slope regression value of 0.114 are selected. If the raw values are equal to or greater than 701 and less than or equal to 850, pathway B and a corresponding Hb predictive value of 67 and Hb slope regression value of 0.114 are selected. If the raw values are equal to or greater than 851 and less than or equal to 950, pathway C and a corresponding Hb predictive value of 81 and Hb slope regression value of 0.114 are selected. If the raw values are equal to or greater than 951 and less than or equal to 1100, pathway D and a corresponding Hb predictive value of 98 and Hb slope regression value of 0.114 are selected. If the raw values are greater than or equal to 1101, pathway E and a corresponding Hb predictive value of 100.5 and Hb slope regression value of 0.114 are selected.

TABLE II

| Pathway | RAW DATA VALUE (X) | Hb PREDICTIVE VALUE | Hb SLOPE REGRESSION VALUE |
| --- | --- | --- | --- |
| A | 500 ≤ X ≤ 700 | 31.5 | 0.114 |
| B | 701 ≤ X ≤ 850 | 67 | 0.114 |
| C | 851 ≤ X ≤ 950 | 81 | 0.114 |
| D | 951 ≤ X ≤ 1100 | 98 | 0.114 |
| E | 1101 ≤ X | 100.5 | 0.114 |

The obtained predictive and slope regression values may then be used to determine a hemoglobin level of the user (912). To determine a hemoglobin level, the wearable diagnostic device may apply a Hb slope regression to the set of raw data and determine values indicative of a hemoglobin level using [Equation 2] as noted below.

$$Hb\text{ value} = ((Hb\text{ Regression Slope})*(\text{Raw data})) - \text{Predictive Values}_{(Hb\text{-clinical sampling regression})} \quad [\text{Equation 2}]$$

The determined hemoglobin value may then be output through various suitable methods (914). For example, the determined hemoglobin value may be output on a display of the wearable diagnostic device or output by a speaker of the wearable diagnostic device.

For raw data values that are less than 500 in the glucose or hemoglobin test, the wearable diagnostic device may determine that the values are erroneous and initiate another attempt to obtain the raw data values through the one or more IR/light/laser sensors. If after three attempts, no values above 500 can be obtained, the wearable diagnostic device may output an error message indicating to the user that a glucose or hemoglobin test cannot be performed at the present time.

When a cholesterol test is being conducted to determine cholesterol levels (e.g., HDL, LDL, Triglyceride molecules) associated with the user wearing the wearable diagnostic device, an inferior part of the user's left wrist is exposed to the infrared signal emitted from the IR/light/laser sensor. This region of the user's skin may also be exposed to a magnetic field for a short period of time, e.g., 10 or 30 seconds, after which blood particles, except for cholesterol molecules, arrange themselves according to positive and negative pole of electromagnetic. Data indicative of the infrared absorption spectra may be obtained (1306) before and after applying the magnetic field and the obtained data may be subsequently processed (1308). The processing of obtained data may include converting the data to a digital signal using an analog to digital converter (ADC), and calculating a difference between the absorption spectra values before and after applying the magnetic field to yield a raw value.

Next, a predicted cholesterol level value is obtained from a database (1310). The database may include a mapping of cholesterol levels to raw values and may be organized according to demographic classes. The database may be generated based on testing of multiple human subjects as described below.

Initially, a subject's demographic profile may be recorded. The demographic profile may include various types of descriptive information about the subject, such as the subject's age, sex, ethnicity, skin color, marital status, and/or medical conditions. For example, a subject may have a demographic profile of a 48-year old Caucasian man, widowed, with skin cancer. For each subject, an invasive cholesterol test may be taken using various suitable methods and the test results may be added to the subject profile.

Next, current and infrared signal measurements of the subject may be obtained using resistive and infrared sensors, respectively, as described above. The current and infrared signal measurements may be taken before a magnetic field is applied and after a magnetic field is applied for a certain period of time. Differential values of the measured signals may be calculated and saved as raw values. The raw values are mapped to cholesterol levels obtained from the invasive cholesterol tests and stored in the subject profile.

Hundreds and thousands of subjects may be tested so that a large sample size of subjects can be used to generate the database that maps raw values to cholesterol levels according to one or more demographic classes (e.g., sex, ethnicity, age, etc.). In some implementations, statistical data may be extracted from the tests so that mean, median, and mode values of cholesterol levels and raw values may be determined for each demographic class.

In general, various types of demographic classes may be formed. For example, in some cases, a demographic class may be limited to age, e.g., an age of people in their 40s. In some cases, a demographic class may include multiple demographic characteristics, such as age and ethnicity or age, ethnicity, and sex. Accordingly, the database may include a mapping table that maps the likely cholesterol levels based on the raw values associated with particular demographic classes. It is noted here that the database can be generated in an anonymous manner such that the identity of subjects is not revealed or known.

Referring back to FIG. 13, the predicted cholesterol level value is obtained (1310) from the database based on the raw values obtained in operation 1308. In particular, a cholesterol level mapped to the raw value obtained in operation 1308 and a demographic profile of the user wearing the wearable diagnostic device is obtained by referring to the mapping table in the database.

Next, the predicted cholesterol level value may be determined to be the likely cholesterol level of the user wearing the wearable diagnostic device (1312). In some implementations, the predicted cholesterol level value may be compared to previously obtained cholesterol levels of the user. If the difference between the predicted cholesterol level and the last obtained cholesterol level of the user is greater than a threshold, e.g., 3%, the wearable diagnostic device may repeat operations 1302 to 1310 to obtain a new predicted cholesterol level. Such an iteration may be continued until a predicted cholesterol level value is within a threshold difference of the last obtained cholesterol level of the user. In some cases, if three iterations are executed without satisfying the threshold difference, the predicted cholesterol level value obtained at the third iteration may be determined as the likely cholesterol level of the user wearing the wearable diagnostic device. The determined likely cholesterol level of the user may then be displayed by display 102 of the wearable diagnostic device.

In the above-noted exemplary implementations, predictive values were utilized to determine glucose, hemoglobin, or cholesterol levels. The predictive values may be determined using various different methods and based on several factors. The method to obtain predictive values for cholesterol levels is described above. The methods to obtain predictive values for glucose and hemoglobin levels is described further with respect to FIGS. 8 and 10.

Figure 8:
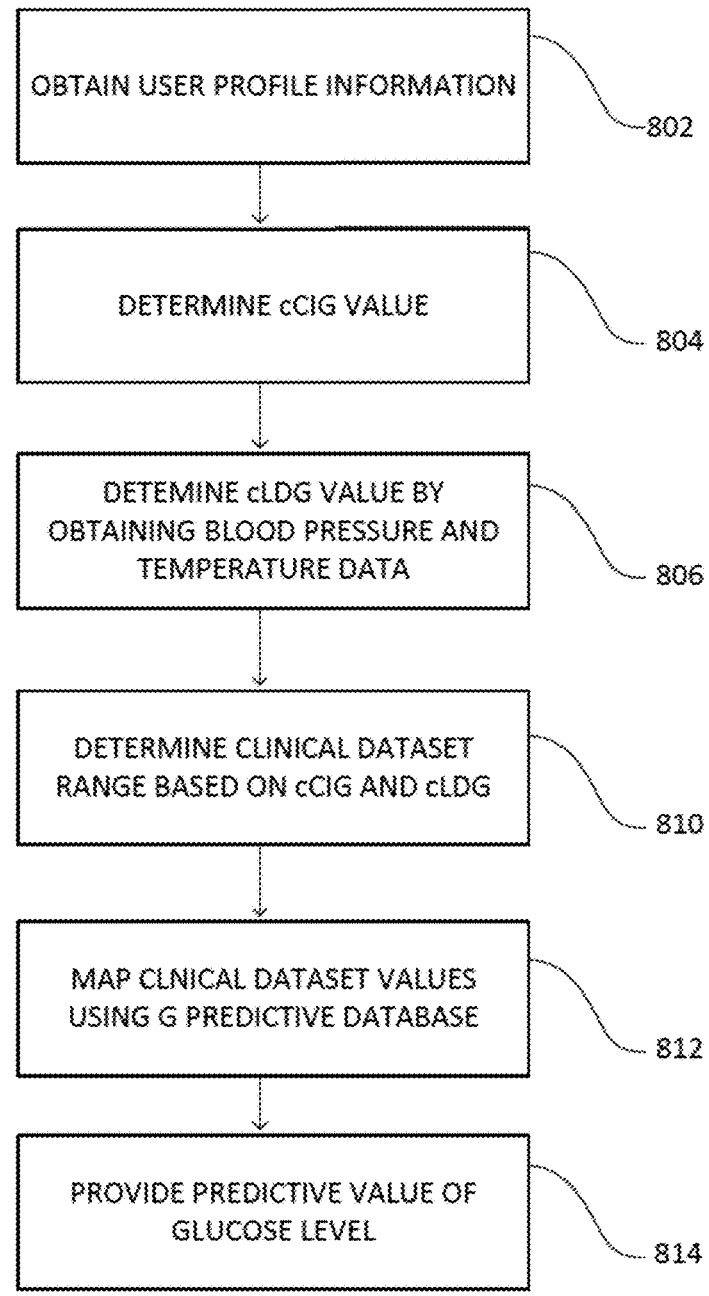
FIG. 8 depicts a flowchart of an exemplary method to determine a glucose predictive value.

Referring to FIG. 8, to obtain a predictive value for the glucose level of a user, the wearable diagnostic device may obtain user profile information (802). The user profile information may include one or more of a user's residential location, a user's doctor, a user's pharmacist, a user's medical record holder, a user's demographic associations with one or more groups, a food diet of the user, an indication of a number of children the user has, a medical history of the user, one or more past or present medical conditions, for example, allergies, surgeries, genetic conditions, of the user, one or more health concerns of the user, and one or more blood content levels the user is interested in obtaining details about.

Using information from the user's profile, the wearable diagnostic device may determine the clinical Correlation Information value for Glucose (cCIG) for the user (804) based on a blood pressure and temperature of the user. In some implementations, the cCIG may be a matrix of values representative of the likely blood pressure and temperature. In general, various suitable methods may be utilized to obtain the blood pressure and temperature of the user. In some implementations, the blood pressure may be obtained as described in this specification with reference to FIGS. 11 and 12, and the temperature may be obtained using a temperature sensor included in the wearable diagnostic device. In some cases, the cCIG may be determined using clinical information obtained from the user profile such as the user's medical history that includes data such as a doctor's report, past or present medical conditions, clinical diagnoses, etc.

Next, the wearable diagnostic device may determine the clinical Linked Demographic value for Glucose (cLDG) for the user (806). The cLDG may be determined, in part, based on one or more user characteristics such as a demographic group of the user, an age of the user, and other personal characteristics of the user. As an example, if the raw value glucose noted above is associated with a particular path, such as path A, or the user profile indicates a particular demographic origin or profile of the user, the cLDG value may be determined in a manner that the cLDG value corresponds to the raw glucose value or particular demographic origin or profile of the user. In some implementations, the cLDG may be a matrix of values representative of various characteristics, e.g., age, diet, gender, of the user, if the user has agreed to provide this personal information.

After obtaining the cCIG and cLDG, the wearable diagnostic device may determine a clinical dataset range based on the cCIG and cLDG (810). The determined clinical dataset range is mapped to a glucose predictive value for the user's glucose level (812). A database storing various clinical dataset ranges and glucose predictive values may be queried with the determined clinical dataset range and may return a glucose predictive value that maps to the determined clinical dataset range. The glucose predictive value may then be provided and utilized for determining the user's glucose level (814).

Figure 10:
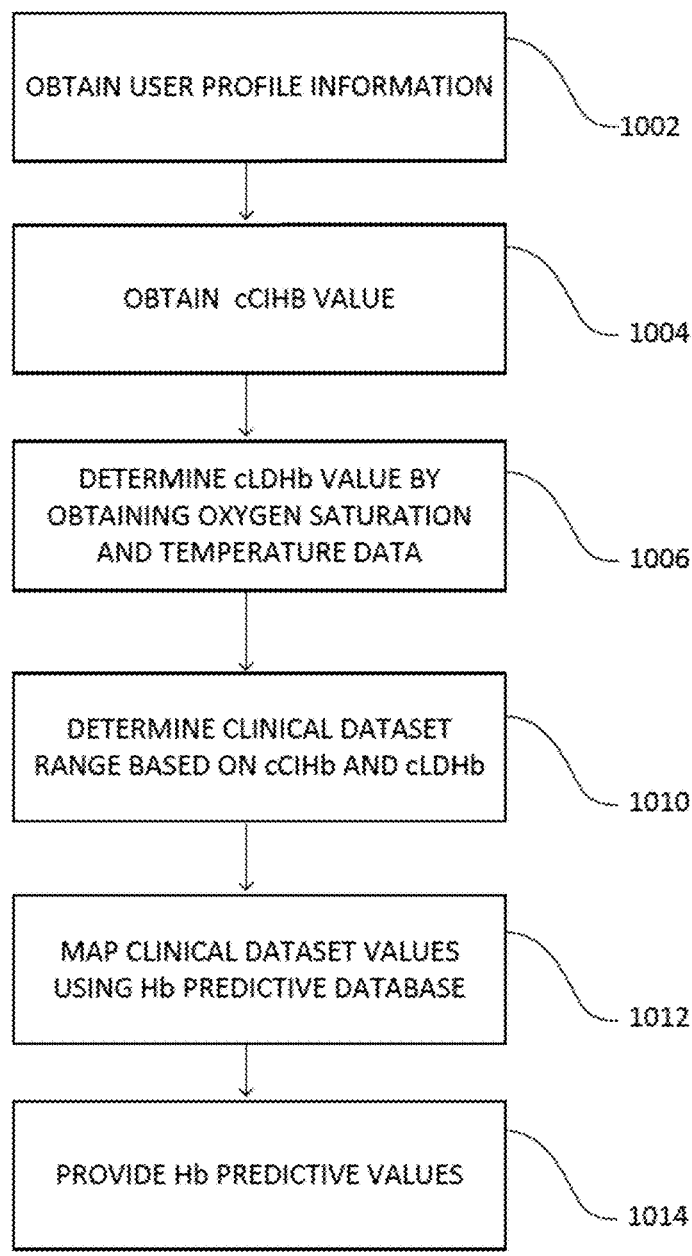
FIG. 10 depicts a flowchart of an exemplary method to determine a hemoglobin predictive value.

Referring to FIG. 10, to obtain a predictive value for the hemoglobin level of a user, the wearable diagnostic device may obtain user profile information (1002). The user profile information may include one or more of a user's residential location, a user's doctor, a user's pharmacist, a user's medical record holder, a user's demographic associations with one or more groups, a food diet of the user, an indication of a number of children the user has, a medical history of the user, one or more past or present medical conditions, for example, allergies, surgeries, genetic conditions, of the user, one or more health concerns of the user, and one or more blood content levels the user is interested in obtaining details about.

Using information from the user's profile, the wearable diagnostic device may determine the clinical Correlation Information value for Hemoglobin (cCIHb) for the user (1004). The cCIHb may be determined using clinical information obtained from the user profile such as the user's medical history that includes data such as a doctor's report, past or present medical conditions, clinical diagnoses, etc. In some implementations, the cCIHb may be a matrix of values representative of various aspects of the user's medical history if the user has agreed to provide this personal information.

Next, the wearable diagnostic device may determine the clinical Linked Demographic value for Hemoglobin (cLDHb) for the user by obtaining oxygen saturation and temperature data of the user (1006). In some implementations, the cLDHb may be a matrix of values representative of the likely oxygen saturation and temperature of the user. In general, various suitable methods may be utilized to obtain the oxygen saturation and temperature of the user. In some implementations, the oxygen saturation may be obtained as described in this specification with reference to FIG. 11, and the temperature may be obtained using a temperature sensor included in the wearable diagnostic device. In some implementations, the cLDHb may be determined, in part, based on information provided by the user profile such as one or more of user characteristics such as a demographic group of the user, an age of the user, and other personal characteristics of the user.

After obtaining the cCIHb and cLDHb, the wearable diagnostic device may determine a clinical dataset range based on the cCIHb and cLDHb (1010). The determined clinical dataset range is mapped to a hemoglobin predictive value for the user's hemoglobin level (1012). A database storing various clinical dataset ranges and hemoglobin predictive values may be queried with the determined clinical dataset range and may return a hemoglobin predictive value that maps to the determined clinical dataset range. The hemoglobin predictive value may then be provided and utilized for determining the user's hemoglobin level (1014).

By utilizing predictive values to determine the user's glucose and hemoglobin levels in addition to utilizing blood pressure and temperature data, the determined glucose and hemoglobin levels of the user have a much higher accuracy relative to methods of determining glucose and hemoglobin levels that do not utilize predictive values. The predictive values include the user's clinical and demographic information and can therefore make calculations that factor in parameters such as skin color and age, which may affect glucose or hemoglobin levels, more accurate. The predictive values may also be used to correlate the predictive values to the user's susceptibility to certain diseases, and the user may thereby take precautionary steps to minimize the probability of acquiring these diseases and to improve the user's health and life expectancy. Furthermore, these multiple tests may be performed and results from the tests may be obtained through a single device upon demand providing the user a high degree of convenience.

Figure 11:
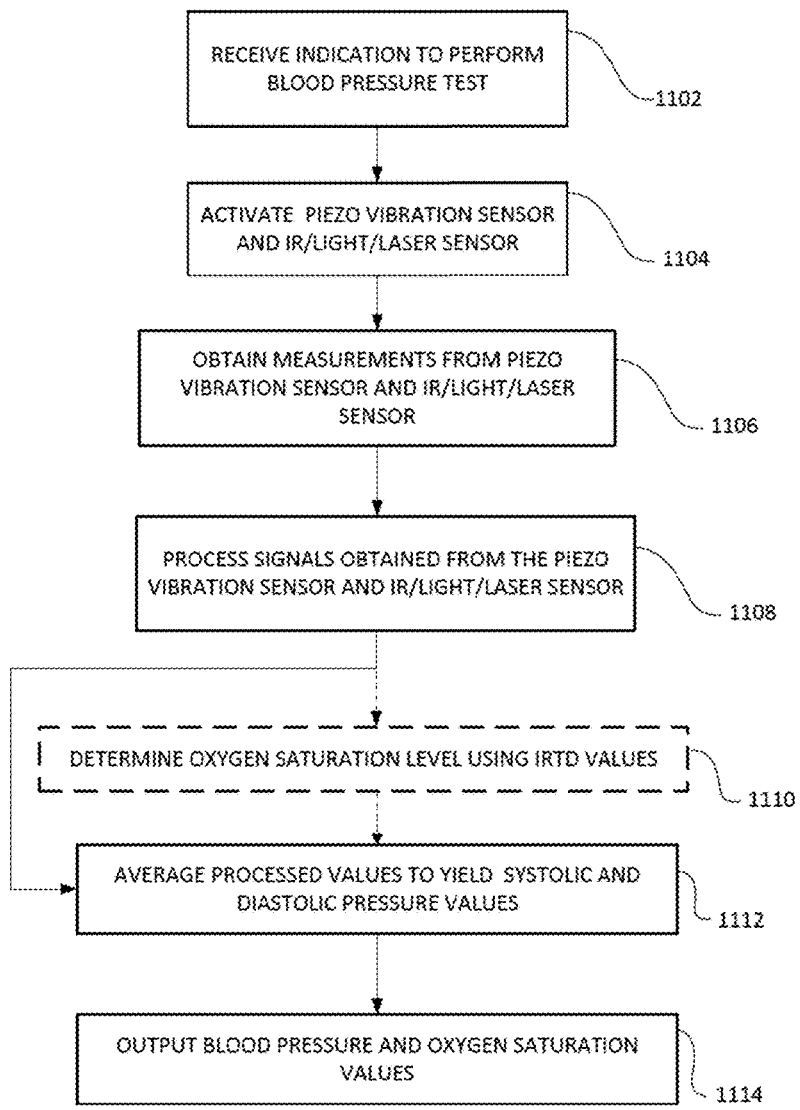
FIG. 11 depicts a flowchart of an exemplary method to determine a Blood Pressure level of a user.

In addition to obtaining the user's glucose and hemoglobin levels, the wearable diagnostic device may determine a user's blood pressure and oxygen saturation level. A flowchart of an exemplary method to determine blood pressure and oxygen saturation levels of a user is depicted in FIG. 11. Initially, the wearable diagnostic device may receive an indication that a blood pressure determination should be performed (1102). The indication that blood pressure determination should be performed may include one or more of a selection made by the user to provide a blood pressure reading and a request made by one or more processors according to a scheduled time. For example, the wearable diagnostic device may be programmed to provide a blood pressure reading at certain times or after certain time periods. The wearable diagnostic device may then schedule days and times when a blood pressure reading should be provided to the user, and may initiate the method to determine blood pressure and oxygen saturation levels at the scheduled times.

After receiving the indication that a blood pressure determination should be performed (1102), the wearable diagnostic device may determine the type of sensor utilized for the blood pressure test and activate the determined type of sensors, which in the case of a blood pressure test may include the piezo vibration sensor and the IR/light/laser sensor (1104). Activating the sensors may include several operations, including but not limited to, providing increased power to the sensors and configuring or calibrating the sensors.

The activated piezo vibration sensor and IR/light/laser sensor may obtain user measurements (1106). For example, the piezo vibration sensor is configured to sense or detect one or more of a movement, position, proximity, speed, and direction of the user's hand, and to generate electric signals corresponding to the detected one or more of the touch, vibration, and shock movements. The IR/light/laser sensor is configured to emit an infrared signal, detect a reflection of the emitted infrared signal from the user's skin. In some implementations, a preamplifier may be used to amplify weak pulse signals obtained through the piezo vibration sensor.

The signals detected by piezo vibration sensor and the IR/light/laser sensor may be processed, for example by performing analog-to-digital conversion (ADC) and filtering operations, to generate an infrared target detection (IRTD) value and a piezo vibration (PV) value (1108). In general, various signal processing operations may be performed on the signals detected by the piezo vibration sensor and the IR/light/laser sensor. In some implementations, operations 1104-1108 may be repeated a plurality of times and average values of the multiple IRTD and PV values may be determined.

The processing may also include comparing the determined IRTD and PV values to predicted IRTD and PV values. The comparison generates two sets of blood pressure values. Each of the two sets of blood pressure values are averaged to yield the systolic and diastolic pressure values respectively (1112). The systolic and diastolic pressure values may be utilized to determine the mean arterial pressure (MAP) using [Equation 3] as noted below.

$$\text{MAP} = \text{Diastolic Pressure} + (1/3)(\text{Systolic Pressure} - \text{Diastolic Pressure}) \quad \text{[Equation 3]}$$

Figure 12:
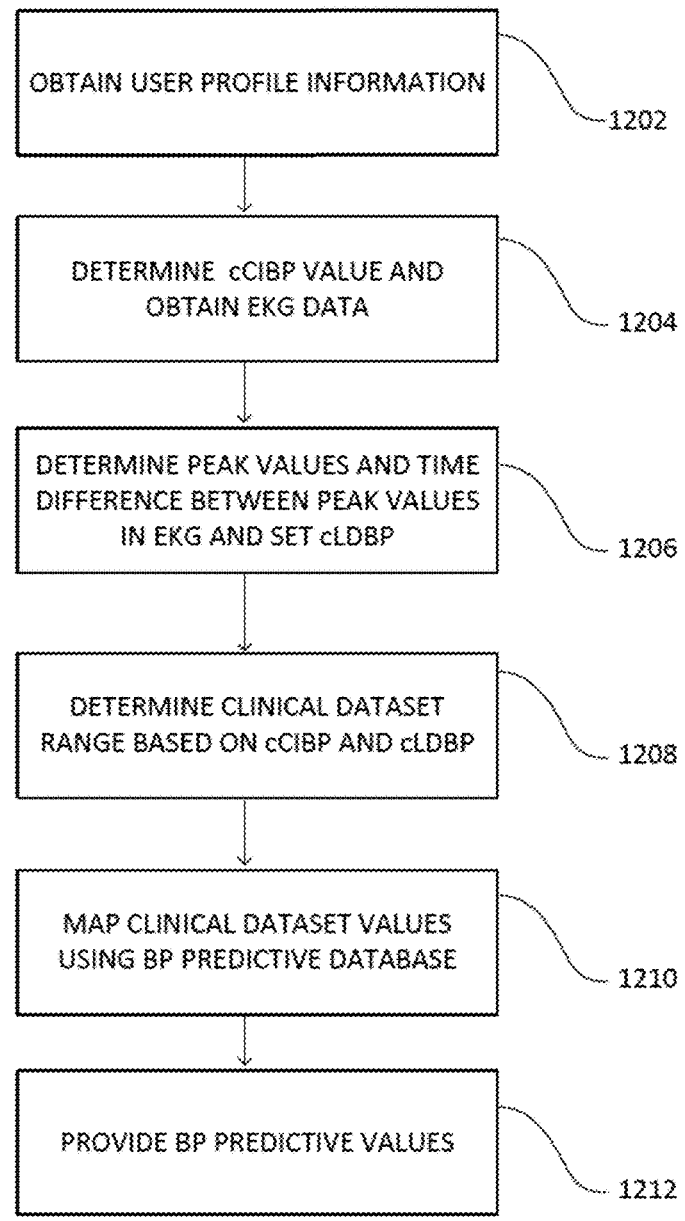
FIG. 12 depicts a flowchart of an exemplary method to determine a Blood Pressure predictive value.

The generation of predicted values for blood pressure measurements is explained below with reference to FIG. 12. In some implementations, an oxygen saturation level of the user's blood may also be determined using [Equation 4] (1110).

$$\text{Oxygen Saturation Level} = ((C_{HbO2})/(C_{HbO2} + C_{Hb}))*100 \quad \text{[Equation 4]}$$

In [Equation 4], $C_{HbO2}$ equals to a concentration of oxygenated hemoglobin, and $C_{Hb}$ equals to a concentration of deoxygenated hemoglobin. The values for $C_{HbO2}$ and $C_{Hb}$ may be obtained by using the infrared sensor.

After operations 1110 and 1112, the blood pressure and oxygen saturation values are output (1114). For example, in some implementations, the blood pressure and oxygen saturation values are displayed by display. In some implementations, the blood pressure and oxygen saturation values are output through an audio speaker. In some implementations, the blood pressure and oxygen saturation values may be communicated to another electronic device using a message, such as an email, SMS, or MMS. The message may be generated and populated automatically without any user input. A user may be prompted to confirm whether the message with the blood pressure and oxygen saturation values should be transmitted to the other electronic device.

In the above-noted exemplary implementations, predictive values were utilized to determine a user's blood pressure. The predictive values may be determined using various different methods and based on several factors. Referring to FIG. 12, to obtain a predictive value for a user's blood pressure, the wearable diagnostic device may obtain user profile information (1202), as described in operations 802 and 1002. The wearable diagnostic device may obtain the user's clinical and demographic information from the user profile.

Using information from the user's profile, the wearable diagnostic device may determine the clinical Correlation Information value for Blood Pressure (cCIBP) for the user and obtain EKG data (1204). The cCIBP may be determined using clinical information obtained from the user profile such as the user's medical history that includes data such as a doctor's report, past or present medical conditions, clinical diagnoses, etc. The EKG data may be obtained from various suitable sources, such as, for example, the user's medical history.

Next, the EKG data is processed to determine peak values and time difference between peak values particularly R wave (1206). The wearable diagnostic device may also determine the clinical Linked Demographic value for Blood Pressure (cLDBP) for the user (1206). In some implementations, one or more processors in the wearable diagnostic device may execute one or more programs and algorithms that detect peak values and time difference between the detected peak values in a user's EKG. In some implementations, the cLDBP may be determined, in part, based on one or more user characteristics such as a demographic group of the user, an age of the user, and other personal characteristics of the user. In some implementations, the cLDBP may be a matrix of values representative of various characteristics, e.g., age, diet, gender, of the user, if the user has agreed to provide this personal information.

After obtaining the cCIBP and cLDBP, the wearable diagnostic device may determine a clinical dataset range based on the cCIBP and cLDBP (1208). The determined clinical dataset range is mapped to a Blood pressure predictive value for the user's glucose level (1210). A database storing various clinical dataset ranges and Blood pressure predictive values may be queried with the determined clinical dataset range and may return a Blood pressure predictive value that maps to the determined clinical dataset range. The Blood pressure predictive value may then be provided and utilized for determining the user's Blood pressure level (1212).

In some implementations, the wearable diagnostic device may execute a process for obtaining an EKG and a heart rate level for the user wearing the wearable diagnostic device.

When the wearable diagnostic device is secured on the user's left arm, a first cardiac electrode may be disposed on or within a bottom surface of the wearable diagnostic device and may be in contact with a superior side of the user's left wrist. A second cardiac electrode is disposed on or within a top surface of the wearable diagnostic device without contacting the skin on the user's left arm. The first cardiac electrode may acquire a signal from the superior part of the user's wrist on the left arm and the second cardiac electrode may acquire two signals with the second cardiac electrode placed on the user's chest. The acquired signals may include cardiac electrical potential waveforms, such as voltages produced during the contraction of the heart. Data obtained from the three signals is converted into Provocation, Quality, Radiation, Severity, Time (PQRST) waves. The PQRST waves may be used to generate Einthoven's triangle, EKG plots, and calculate additional information, such as the user's heartbeat. In some cases, the PQRST waves may be used to diagnose cardiac conditions.

In some implementations, the wearable diagnostic device may execute a process for obtaining a body temperature associated with the user wearing the wearable diagnostic device. After the wearable diagnostic device is wrapped around a user's arm and is in contact with the user's skin, the temperature sensor in the wearable diagnostic device will obtain a temperature of the user based on the skin contact. For example, the temperature sensor may contact the wrist, and may obtain the user's body temperature data over a particular period of time. The temperature sensor provides the sensor data to one or more processors, which may convert the received data to the Fahrenheit scale and average the temperature data taken over one or more periods to yield a likely body temperature of the user.

In some implementations, the wearable diagnostic device may execute a process for obtaining a hand vibration associated with the user wearing the wearable diagnostic device. One or more processors may execute operations with a timer and accelerometer or piezo vibration sensor to obtain hand vibration measurements. For example, after receiving an indication that a user is interested in viewing information regarding hand vibration, a processor may set the timer for a particular time period, for example, 60 seconds, and instruct the accelerometer or piezo vibration sensor to obtain vibration data for the particular time period. The accelerometer or piezo vibration sensor may sense the number and strength of hand vibrations of the user in the particular time period, and provide data indicative of the number of vibrations to the processor.

The processor may receive the data indicative of the number of vibrations and may determine a frequency of the vibrations. If the vibrations have a frequency between 3-7 Hertz (Hz), the vibrations may be classified as vibrations associated with Parkinson's tremors. The processor may also obtain amplitude information from the accelerometer or piezo vibration sensor to determine the strength of any vibrations associated with the Parkinson's tremors. Data indicative of the timing, strength, and frequency of the vibrations may be stored in a user profile in a storage device and/or may be presented to the user via display.

The processes described above to obtain information regarding a user's glucose levels, hemoglobin levels, blood pressure level, EKG, heart rate levels, body temperature, hand vibrations, and cholesterol levels may be executed in parallel, simultaneously, or at different times. The wearable diagnostic device has sufficient processing power to execute any of these processes at any time and in response to a user request.

In some implementations, multiple diagnostic tests may be run sequentially or simultaneously. For example, EKG tests may be conducted before or during a Blood pressure test. An oxygen saturation test and body temperature test may be conducted before or during a hemoglobin test. A blood pressure test and body temperature test may be conducted before or during a glucose test. Other variations and combinations are possible. As an example, if a user has a medical history of certain conditions such as being a diabetic, the wearable diagnostic device may periodically conduct a test that is most relevant to the user's condition, such as a glucose diagnostic test, and may conduct other tests, such as a blood pressure test, cholesterol test, or oxygen saturation test, before, after, or during the most relevant diagnostic test.

In some implementations, although the user may input a request to perform one type of diagnostic test, e.g., a glucose test, the wearable diagnostic device may determine one or more tests, e.g., a blood pressure test, that are to be conducted along with the user requested diagnostic test. The additional tests may be determined based on one or more criterion such as, for example, tests that are frequently selected to be conducted simultaneously, sequentially, or in pairs by the user, by a default setting, by the manufacturer's settings, by a doctor's recommendation. In some implementations, the additional tests may be determined based on a user's medical history. For example, if a user suffers from diabetes and high blood pressure, whenever the user selects a blood pressure test, the wearable diagnostic device may also conduct a glucose test. If the user selects a glucose test, the wearable diagnostic device may also conduct a blood pressure test.

Results obtained from executing one or more of the processes described above can be stored in a memory in the wearable diagnostic device or stored in a database or cloud account associated with the user. Results obtained from executing one or more of the processes described above may also be displayed through display. In some implementations, the wearable diagnostic device may output a visual, audio, or electronic alarm if one or more of the determined glucose levels, hemoglobin levels, blood pressure level, EKG, heart rate levels, body temperature and hand vibrations indicate a serious medical condition. For instance, the wearable diagnostic device may generate an audio output, such as a sound wave, recommending the user go to a doctor if, for example, the EKG includes some abnormal heart movement signs or the body temperature is above 102 degrees Fahrenheit.

It should be understood that implementations and/or actions described in this specification may be implemented in digital electronic circuitry, or in computer software, firmware, or hardware, including the structures disclosed in this specification and their structural equivalents, or in combinations of one or more of them. Implementations may be implemented as one or more computer program products, e.g., one or more modules of computer program instructions encoded on a computer readable medium for execution by, or to control the operation of, data processing apparatus. The computer readable medium may be a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers. The apparatus may include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal that is generated to encode information for transmission to suitable receiver apparatus.

A computer program (also known as a program, software, software application, script, or code) may be written in any form of programming language, including compiled or interpreted languages, and it may be deployed in any form, including as a standalone program or as a module, component, subroutine, or other unit suitable for use in a computing environment. A computer program does not necessarily correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may be executed on one computer or on multiple computers that are located at one site or distributed across multiple sites and interconnected by a communication network.

The processes and logic flows described in this specification may be performed by one or more programmable processors executing one or more computer programs to perform actions by operating on input data and generating output. The processes and logic flows may also be performed by, and apparatus may also be implemented as, special purpose logic circuitry, e.g., an FPGA (field programmable gate array) or an ASIC (application specific integrated circuit).

Processors in computers that execute a computer program include, by way of example, both general and special purpose microprocessors, and any one or more processors of any kind of digital computer. Generally, a processor will receive instructions and data from a read only memory or a random access memory or both.

While this specification contains many specifics, these should not be construed as limitations on the scope of the disclosure or of what may be claimed, but rather as descriptions of features specific to particular embodiments. Certain features that are described in this specification in the context of separate embodiments may also be implemented in combination in a single embodiment. Conversely, various features that are described in the context of a single embodiment may also be implemented in multiple embodiments separately or in any suitable sub-combination. Moreover, although features may be described above as acting in certain combinations and may even be claimed as such, one or more features from a claimed combination may, in some cases, be excised from the combination, and the claimed combination may be directed to a sub-combination or variation of a sub-combination.

It should be understood that the phrase one or more of and the phrase at least one of include any combination of elements. For example, the phrase one or more of A and B includes A, B, or both A and B. Similarly, the phrase at least one of A and B includes A, B, or both A and B.

Thus, particular implementations have been described. Other implementations are within the scope of the following claims. For example, the actions recited in the claims may be performed in a different order and still achieve desirable results.

What is claimed is:

1. A system comprising:
   one or more sensors configured to detect one or more characteristics of a user;

one or more analog-to digital converters coupled to the one or more sensors and configured to digitize one or more analog signals; and one or more computer devices and one or more storage devices storing instructions which when executed by the one or more computer devices, cause the one or more computer devices to perform operations comprising:

receiving data indicative of a request to perform a non-invasive diagnostic test to detect a medical state of the user;

obtaining information associated with the user to create a user profile;

controlling one or more infrared laser sensors of the one or more sensors to respectively emit one or more infrared signals towards a body part of the user;

receiving, through the one or more infrared laser sensors, one or more infrared signals reflected from the body part of the user;

determining an absorption pattern based on the received one or more infrared signals;

digitizing, using the one or more analog-to digital converters, the absorption pattern;

selecting, from among a plurality of data sets stored on the one or more storage devices, a particular data set corresponding to the digitized absorption pattern;

communicating, over one or more computer networks with one or more databases, to obtain a predictive value for the non-invasive diagnostic test, the predictive value corresponding to a likely result of the requested non-invasive diagnostic test for a demographic group to which the user belongs, an indication of the demographic group being provided by the user profile;

determining a result of the non-invasive diagnostic test for the user based on the (i) predictive value corresponding to the likely result of the non-invasive diagnostic test for the demographic group to which the user belongs, and (ii) the selected particular data set; and outputting, through a display or a speaker, the result for the non-invasive diagnostic test.

2. The system of claim 1, wherein the non-invasive diagnostic test comprises one or more of a glucose test, a cholesterol test, a hemoglobin test, an oxygen saturation level test, and an electrocardiogram monitoring test.

3. The system of claim 1, wherein the selecting, from among the plurality of data sets, the particular data set corresponding to the digitized absorption pattern comprises:
generating raw data from the digitized absorption pattern;
selecting a pathway based on the raw data; and
obtaining the particular data set and the predictive value according to the selected pathway; and
wherein the particular data set comprises a regression value.

4. The system of claim 1, wherein the operations further comprise:
obtaining user clinical data and user demographic data from the one or more databases;
determining a clinical dataset range based on the obtained user clinical data and the user demographic data; and
mapping the clinical dataset range to the predictive value for the non-invasive diagnostic test.

5. The system of claim 1, wherein the one or more sensors comprise one or more of a wireless cardiac electrode, a piezo vibration sensor, an infrared sensor, a temperature sensor, an accelerometer, and a micro-electro mechanical system (MEMS) sensor.

6. The system of claim 1, wherein the operations further comprise:
determining a second non-invasive diagnostic test to be conducted based on (i) a user pattern of associating the second non-invasive diagnostic test with the non-invasive diagnostic test, and (ii) a medical history of the user;
activating a second set of one or more sensors based on the second non-invasive diagnostic test;
receiving second infrared signals through the second set of one or more sensors;
determining a second absorption pattern based on the received second infrared signals;
digitizing, using the one or more analog-to digital converters, the second absorption pattern;
selecting, from among the plurality of data sets stored on the one or more storage devices, a second particular data set corresponding to the digitized second absorption pattern;
communicating, over the one or more computer networks with the one or more databases, to obtain a second predictive value for the second non-invasive diagnostic test, the second predictive value corresponding to a likely result of the requested second non-invasive diagnostic test for the demographic group to which the user belongs; and
determining a second result of the second non-invasive diagnostic test for the user based on (i) the second predictive value corresponding to the likely result of the second non-invasive diagnostic test for the demographic group to which the user belongs, and (ii) the selected second particular data set.

7. The system of claim 6, wherein obtaining the predictive value for the non-invasive diagnostic test comprises determining the predictive value for the non-invasive diagnostic test using the second test result.

8. The system of claim 6, wherein the second non-invasive diagnostic test is a cholesterol test conducted simultaneously as the non-invasive diagnostic test that is a glucose test.

9. The system of claim 6, wherein the system comprises a watch configured to conduct a non-invasive diagnostic test and the second non-invasive diagnostic test, the watch including the one or more computer devices.

10. A computer-implemented method comprising:
receiving, at a device configured to be worn by a user, data indicative of a request to perform a non-invasive diagnostic test to detect a medical state of the user;
obtaining, by one or more computer devices in the device, information associated with the user to create a user profile;
controlling, by the one or more computer devices in the device, one or more infrared laser sensors to respectively emit one or more infrared signals towards a body part of the user;
receiving, through the one or more infrared laser sensors, one or more infrared signals reflected from the body part of the user;
determining, by the one or more computer devices, an absorption pattern based on the received one or more infrared signals;
digitizing, using one or more analog-to digital converters in the device, the absorption pattern;

selecting, by the one or more computer devices and from among a plurality of data sets stored on one or more storage devices, a particular data set corresponding to the digitized absorption pattern;

communicating, by the one or more computer devices and over one or more computer networks with one or more databases, a predictive value for the non-invasive diagnostic test, the predictive value corresponding to a likely result of the requested non-invasive diagnostic test for a demographic group to which the user belongs, an indication of the demographic group being provided by the user profile;

determining, by the one or more computer devices, a result of the non-invasive diagnostic test for the user based on the (i) predictive value corresponding to the likely result of the non-invasive diagnostic test for the demographic group to which the user belongs, and (ii) the selected particular data set; and outputting, by the one or more computer devices through a display or a speaker in the device, the result for the non-invasive diagnostic test.

11. The computer-implemented method of claim 10, wherein the non-invasive diagnostic test comprises one or more of a glucose test, a cholesterol test, a hemoglobin test, an oxygen saturation level test, and an electrocardiogram monitoring test.

12. The computer-implemented method of claim 10, wherein the selecting, from among the plurality of data sets, the particular data set corresponding to the digitized absorption pattern comprises:

generating raw data from the digitized absorption pattern;
selecting a pathway based on the raw data; and
obtaining the particular data set and the predictive value according to the selected pathway; and
wherein the particular data set comprises a regression value.

13. The computer-implemented method of claim 10, wherein the operations further comprise:
obtaining user clinical data and user demographic data from the one or more databases;
determining a clinical dataset range based on the obtained user clinical data and the user demographic data; and
mapping the clinical dataset range to the predictive value for the non-invasive diagnostic test.

14. The computer-implemented method of claim 10, wherein the one or more sensors comprise one or more of a wireless cardiac electrode, a piezo vibration sensor, an infrared sensor, a temperature sensor, an accelerometer, and a micro-electro mechanical system (MEMS) sensor.

15. The computer-implemented method of claim 10, wherein the operations further comprise:

determining a second non-invasive diagnostic test to be conducted based on (i) a user pattern of associating the second non-invasive diagnostic test with the non-invasive diagnostic test, and (ii) a medical history of the user;
activating a second set of one or more sensors based on the second non-invasive diagnostic test;
receiving second infrared signals through the second set of one or more sensors;
determining a second absorption pattern based on the received second infrared signals;
digitizing, using the one or more analog-to digital converters, the second absorption pattern;

selecting, from among the plurality of data sets stored on the one or more storage devices, a second particular data set corresponding to the digitized second absorption pattern;
communicating, over the one or more computer networks with the one or more databases, to obtain a second predictive value for the second non-invasive diagnostic test, the second predictive value corresponding to a likely result of the requested second non-invasive diagnostic test for the demographic group to which the user belongs; and
determining a second result of the second non-invasive diagnostic test for the user based on (i) the second predictive value corresponding to the likely result of the second non-invasive diagnostic test for the demographic group to which the user belongs, and (ii) the selected second particular data set.

16. The computer-implemented method of claim 15, wherein obtaining the predictive value for the non-invasive diagnostic test comprises determining the predictive value for the non-invasive diagnostic test using the second test result.

17. The computer-implemented method of claim 15, wherein the second non-invasive diagnostic test is a cholesterol test conducted simultaneously as the non-invasive diagnostic test that is a glucose test.

18. The computer-implemented method of claim 15, wherein the non-invasive diagnostic test and the second non-invasive diagnostic test are conducted by a watch including the one or more computer devices.

19. A non-transitory computer-readable storage medium comprising instructions, which, when executed by one or more computers, cause the one or more computers to perform actions comprising:

receiving, at a device configured to be worn by a user, data indicative of a request to perform a non-invasive diagnostic test to detect a medical state of the user;
obtaining information associated with the user to create a user profile;
controlling one or more infrared laser sensors in the device to respectively emit one or more infrared signals towards a body part of the user;
receiving, through the one or more infrared laser sensors, one or more infrared signals reflected from the body part of the user;
determining an absorption pattern based on the received one or more infrared signals;
digitizing, using one or more analog-to digital converters in the device, the absorption pattern;
selecting, from among a plurality of data sets stored on one or more storage devices, a particular data set corresponding to the digitized absorption pattern;
communicating, over one or more computer networks with one or more databases, a predictive value for the non-invasive diagnostic test, the predictive value corresponding to a likely result of the requested non-invasive diagnostic test for a demographic group to which the user belongs, an indication of the demographic group being provided by the user profile;
determining a result of the non-invasive diagnostic test for the user based on the (i) predictive value corresponding to the likely result of the non-invasive diagnostic test for the demographic group to which the user belongs, and (ii) the selected particular data set; and
outputting, by a display or a speaker in the device, the result for the non-invasive diagnostic test.

20. The non-transitory computer-readable storage medium of claim 19, wherein the operations further comprise:

determining a second non-invasive diagnostic test to be conducted based on (i) a user pattern of associating the second non-invasive diagnostic test with the non-invasive diagnostic test, and (ii) a medical history of the user;

activating a second set of one or more sensors based on the second non-invasive diagnostic test;

receiving second infrared signals through the second set of one or more sensors;

determining a second absorption pattern based on the received second infrared signals;

digitizing, using the one or more analog-to digital converters, the second absorption pattern;

selecting, from among the plurality of data sets stored on the one or more storage devices a second particular data set corresponding to the digitized second absorption pattern;

communicating, over the one or more computer networks with the one or more databases, to obtain a second predictive value for the second non-invasive diagnostic test, the second predictive value corresponding to a likely result of the requested second non-invasive diagnostic test for the demographic group to which the user belongs; and determining a second result of the second non-invasive diagnostic test for the user based on (i) the second predictive value corresponding to the likely result of the second non-invasive diagnostic test for the demographic group to which the user belongs, and (ii) the selected second particular data set.

\* \* \* \* \*